(12) United States Patent
Okazoe et al.

(10) Patent No.: US 6,747,174 B2
(45) Date of Patent: Jun. 8, 2004

(54) PROCESSES FOR THE PREPARATION OF FLUORINATED ACYL FLUORIDES AND FLUORINATED VINYL ETHERS

(75) Inventors: Takashi Okazoe, Yokohama (JP); Kunio Watanabe, Yokohama (JP); Masahiro Ito, Yokohama (JP); Daisuke Shirakawa, Yokohama (JP); Shin Tatematsu, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/352,166

(22) Filed: Jan. 28, 2003

(65) Prior Publication Data

US 2003/0146103 A1 Aug. 7, 2003

Related U.S. Application Data

(63) Continuation of application No. PCT/JP01/06460, filed on Jul. 26, 2001.

(30) Foreign Application Priority Data

Jul. 28, 2000 (JP) ......................... 2000-229521

(51) Int. Cl.[7] ................. C07C 51/58; C07C 43/30; C07C 43/32
(52) U.S. Cl. .............. 562/852; 562/840; 562/849; 562/851; 568/592; 568/591; 568/594; 568/596; 568/598; 570/140; 570/142
(58) Field of Search ............... 562/840, 849, 562/851, 852; 570/140, 142; 568/591, 592, 594, 596, 598

(56) References Cited

U.S. PATENT DOCUMENTS

| | | | |
|---|---|---|---|
| 3,475,456 A | 10/1969 | Selman | |
| 5,093,432 A | 3/1992 | Bierschenk et al. | |
| 5,322,903 A | 6/1994 | Bierschenk et al. | |
| 5,466,877 A | 11/1995 | Moore | |
| 6,255,536 B1 | 7/2001 | Worm et al. | |

FOREIGN PATENT DOCUMENTS

| | | |
|---|---|---|
| JP | 5-339255 | 12/1993 |
| WO | WO 01/46093 | 6/2001 |
| WO | WO 02/10108 | 2/2002 |
| WO | WO 02/26686 | 4/2002 |
| WO | WO 02/26688 | 4/2002 |
| WO | WO 02/26689 | 4/2002 |
| WO | WO 02/40437 | 5/2002 |
| WO | WO 02/44138 | 6/2002 |
| WO | WO 02/055471 | 7/2002 |

OTHER PUBLICATIONS

U.S. patent application Ser. No. 10/372,765, Okazoe et al., filed Feb. 26, 2003.
U.S. patent application Ser. No. 10/307,388, Okazoe et al., filed Dec. 2, 2002.
U.S. patent application Ser. No. 10/397,423, Watanabe et al., filed Mar. 27, 2003.
U.S. patent application Ser. No. 10/397,230, Okazoe et al., filed Mar. 27, 2003.
U.S. patent application Ser. No. 10/397,521, Okazoe et al., filed Mar. 27, 2003.

Primary Examiner—Johann Richter
Assistant Examiner—Elvis O. Price
(74) Attorney, Agent, or Firm—Oblon, Spivak, McClelland, Maier & Neustadt, P.C.

(57) ABSTRACT

The present invention provides novel processes for preparing a fluorinated acyl fluoride and a fluorinated vinyl ether.

Namely, it provides a process for preparing a fluorinated acyl fluoride (3), which comprises reacting a compound (1) having a fluorine content of 30 mass % or above with fluorine in a liquid phase to form a compound (2) and then dissociating the ester bond in the compound (2), and a process for preparing a fluorinated vinyl ether (10), which comprises pyrolyzing the fluorinated acyl fluoride:

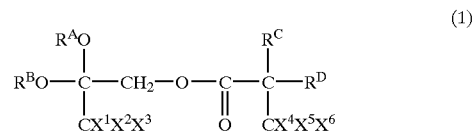

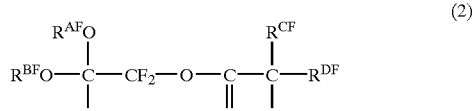

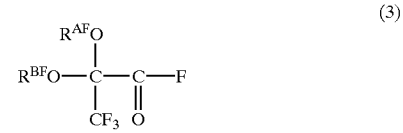

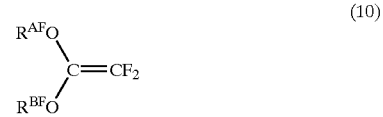

wherein $R^A$ and $R^B$ are alkyl groups or the like, or the combination $R^A$ and $R^B$ is an ethereal oxygen-containing alkylene group or the like, $R^C$ and $R^D$ are perfluoro(ethereal oxygen-containing alkyl) groups or the like, or the combination of $R^C$ and $R^D$ is a perfluoro(ethereal oxygen-containing alkylene) group or the like, $X^1$, $X^2$, $X^3$, $X^4$, $X^5$ and $X^6$ are hydrogen atoms, fluorine atoms or the like, $R^{AF}$, $R^{BF}$, $R^{CF}$ and $R^{DF}$ are groups derived respectively from $R^A$, $R^B$, $R^C$ and $R^D$ by replacing substantially all of the hydrogen atoms by fluorine atoms.

17 Claims, No Drawings

PROCESSES FOR THE PREPARATION OF FLUORINATED ACYL FLUORIDES AND FLUORINATED VINYL ETHERS

TECHNICAL FIELD

The present invention relates to a process for preparing a fluorinated acyl fluoride and a process for preparing a fluorinated vinyl ether from the fluorinated acyl fluoride.

BACKGROUND ART

As techniques for fluorinating compounds containing C—H bonds by converting all the C—H bonds to C—F bonds, use of cobalt trifluoride, direct fluorination with fluorine gas and electrochemical fluorination using hydrogen fluoride electrolytically obtained from electrolytic cells as the fluorine source (hereinafter referred to as ECF) have been known.

These fluorination techniques are applied to give various useful fluorinated compounds. As an example of production of fluorinated acyl fluorides highly useful as intermediates of fluorinated compounds by ECF, production of perfluoroacyl fluorides by ECF of partially fluorinated esters obtained from primary or secondary alcohols and fluorinated acyl fluorides followed by dissociation of the resulting perfluoroesters is disclosed (U.S. Pat. No. 3,900,372).

Liquid phase fluorination in which a hydrogen-containing organic compound dispersed or dissolved in a perhalogenated liquid medium is fluorinated with fluorine gas blown into the medium is disclosed as a fluorination method using direct fluorination (U.S. Pat. No. 5,093,432 and JP-A-4-500520).

However, use of ether oxygen-containing compounds as the substrate in synthesis of fluorinated acyl fluorides by ECF has a problem of very low yields due to cleavage of the C—O bonds. Use of ether oxygen-containing compounds containing no fluorine atoms as the substrate in liquid phase fluorination also has problems of poor yields of fluorinated products and poor volume efficiency.

The present invention aims to solve the problems with the prior art and provides a production process which permits efficient fluorination, even if the substrate is an ether oxygen-containing compound, with a high yield of fluorinated acyl fluorides. The present invention also provides a process for industrially preparing fluorinated acyl fluorides by employing ether oxygen-containing compounds having a specific structure. Further, the present invention provides a process for preparing fluorinated vinyl ethers useful as starting materials for fluororesins.

DISCLOSURE OF THE INVENTION

The present inventors have found out that use of compounds having a fluorine content at or higher than a certain level in liquid phase fluorination as a starting material to produce fluorinated acyl fluorides makes it possible to carry out fluorination at high yield with high volume efficiency, even if the starting material is an ether oxygen-containing compound. They have also found out that pyrolysis of the fluorinated acyl fluoride obtained by the process of the present invention gives fluorinated vinyl ethers useful as starting materials for production of fluororesins.

Namely, the present invention provides a process for preparing a fluorinated acyl fluoride represented by the following formula (3), which comprises reacting a compound represented by the following formula (1) having a fluorine content of 30 mass % or above with fluorine in a liquid phase to form a compound represented by the following formula (2) and then dissociating the ester bond in the compound represented by the formula (2):

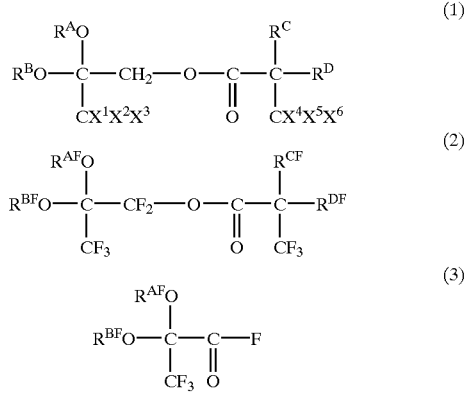

wherein each of $R^A$ and $R^B$, which may be the same or different, is a monovalent saturated hydrocarbon group, a halogenated monovalent saturated hydrocarbon group, a hetero atom-containing monovalent saturated hydrocarbon group or a halogenated (hetero atom-containing monovalent saturated hydrocarbon) group, each of $R^C$ and $R^D$, which may be the same or different, is a hydrogen atom, a halogen atom, a monovalent saturated hydrocarbon group, a halogenated monovalent saturated hydrocarbon group, a hetero atom-containing monovalent saturated hydrocarbon group or a halogenated (hetero atom-containing monovalent saturated hydrocarbon) group, each of $X^1$, $X^2$, $X^3$, $X^4$, $X^5$ and $X^6$, which may be the same or different, is a hydrogen atom or a fluorine atom, provided that at least one of $R^A$, $R^B$, $R^C$, $R^D$, $X^1$, $X^2$, $X^3$, $X^4$, $X^5$ and $X^6$ is a fluorine-containing group or a fluorine atom, $R^{AF}$ corresponds to $R^A$, $R^{BF}$ corresponds to $R^B$, $R^{CF}$ corresponds to $R^C$, $R^{DF}$ corresponds to $R^D$, and when $R^A$, $R^B$, $R^C$ and $R^D$ are hydrogen-containing groups, $R^{AF}$, $R^{BF}$, $R^{CF}$ and $R^{DF}$ are groups derived respectively from $R^A$, $R^B$, $R^C$ and $R^D$ by replacing substantially all the hydrogen atoms by fluorine atoms, and when $R^A$, $R^B$, $R^C$ and $R^D$ are groups containing no hydrogen atoms, $R^{AF}$, $R^{BF}$, $R^{CF}$ and $R^{DF}$ are the same as $R^A$, $R^B$, $R^C$ and $R^D$, respectively, the combination of $R^A$ and $R^B$ and the combination of $R^C$ and $R^D$ may form bivalent groups selected from bivalent saturated hydrocarbon groups, halogenated bivalent saturated hydrocarbon groups, hetero atom-containing bivalent saturated hydrocarbon groups and halogenated (hetero atom-containing bivalent saturated hydrocarbon) groups, respectively, the combination of $R^{AF}$ and $R^{BF}$ forms a bivalent group corresponding to a bivalent group formed by the combination of $R^A$ and $R^B$, and the combination of $R^{CF}$ and $R^{DF}$ forms a bivalent group corresponding to a bivalent group formed by the combination of $R^C$ and $R^D$, provided that when the combination of $R^A$ and $R^B$ and the combination of $R^C$ and $R^D$ form hydrogen-containing bivalent groups, the bivalent groups formed by the combination of $R^{AF}$ and $R^{BF}$ and the combination of $R^{CF}$ and $R^{DF}$ are groups derived from the hydrogen-containing bivalent groups by replacing substantially all the hydrogen atoms by fluorine atoms, and when the combination of $R^A$ and $R^B$ and the combination of $R^C$ and $R^D$ form bivalent groups containing no hydrogen atoms, the bivalent groups formed by the combination of $R^{AF}$ and $R^{BF}$ and the combination of $R^{CF}$ and $R^{DF}$ are the same as the bivalent groups containing no hydrogen atoms.

The present invention also provides a process for preparing a fluorinated acyl fluoride represented by the following formula (3), which comprises reacting a compound represented by the following formula (5) with a compound represented by the following formula (7) to form a compound represented by the following formula (8) having a fluorine content of 30 mass % or above, fluorinating the compound represented by the formula (8) in a liquid phase to form a compound represented by the following formula (9) and dissociating the ester bond in the compound represented by the formula (9):

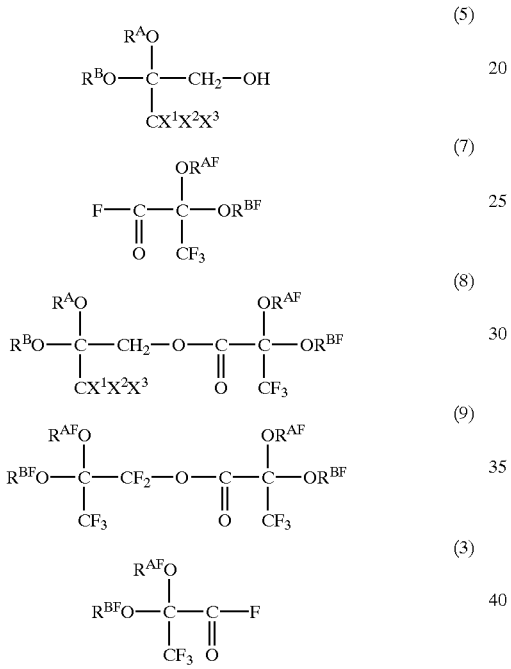

wherein each of $R^A$ and $R^B$, which may be the same or different, is a monovalent saturated hydrocarbon group, a halogenated monovalent saturated hydrocarbon group, a hetero atom-containing monovalent saturated hydrocarbon group or a halogenated (hetero atom-containing monovalent saturated hydrocarbon) group, each of $X^1$, $X^2$ and $X^3$, which may be the same or different, is a hydrogen atom or a fluorine atom, provided that at least one of $R^A$, $R^B$, $X^1$, $X^2$ and $X^3$ is a fluorine-containing group or a fluorine atom, $R^{AF}$ corresponds to $R^A$, $R^{BF}$ corresponds to $R^B$, and when $R^A$ and $R^B$ are hydrogen-containing groups, $R^{AF}$ and $R^{BF}$ are groups derived respectively from $R^A$ and $R^B$ by replacing substantially all the hydrogen atoms by fluorine atoms, and when $R^A$ are $R^B$ are groups containing no hydrogen atoms, $R^{AF}$ and $R^{BF}$ are the same as $R^A$ and $R^B$, respectively, the combination of $R^A$ and $R^B$ may form a bivalent group selected from a bivalent saturated hydrocarbon group, a halogenated bivalent saturated hydrocarbon group, a hetero atom-containing bivalent saturated hydrocarbon group and a halogenated (hetero atom-containing bivalent saturated hydrocarbon) group, provided that when the combination of $R^A$ and $R^B$ forms a hydrogen-containing bivalent group, the bivalent group formed by the combination of $R^{AF}$ and $R^{BF}$ is a group derived from the hydrogen-containing bivalent group by replacing substantially all the hydrogen atoms by fluorine atoms, and when the combination of $R^A$ and $R^B$ forms a bivalent group containing no hydrogen atoms, the bivalent group formed by the combination of $R^{AF}$ and $R^{BF}$ is the same as the bivalent group containing no hydrogen atoms.

The present invention further provides a process for preparing a fluorinated vinyl ether, which comprises pyrolyzing the fluorinated acyl fluoride represented by the following formula (3) obtained by the above-mentioned process to form a compound represented by the following formula (10):

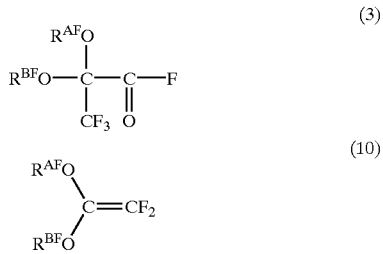

wherein $R^{AF}$ and $R^{BF}$ are the same as defined above.

The present invention still further provides a compound represented by the following formula (11) or (12):

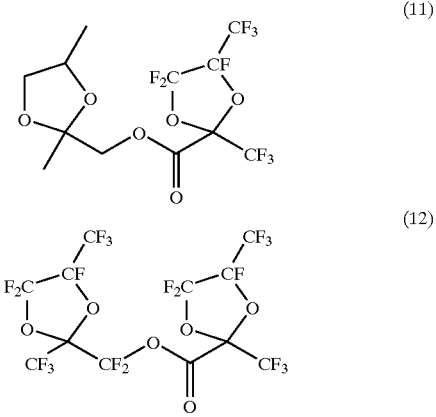

BEST MODE FOR CARRYING OUT THE INVENTION

In the present specification, a compound represented by the formula (1) is expressed as a compound (1). Other compounds will be expressed similarly. As the halogen atom, a fluorine atom, a bromine atom, a chlorine atom or an iodine atom may be mentioned.

In the present invention, a step of reacting a compound (1) with fluorine in a liquid phase (hereinafter referred to as a fluorination step) is carried out first to give a compound (2).

A monovalent saturated hydrocarbon group in the compound (1) may have a linear, branched, cyclic or a partially cyclic structure. The number of carbon atoms in a monovalent saturated hydrocarbon group is preferably from 1 to 20, in particular from 1 to 10, though there is no particular restriction. As a monovalent saturated hydrocarbon, for example, a methyl group, an ethyl group, a propyl group, a butyl group, an isopropyl group, an isobutyl group, a sec-butyl group, a tert-butyl group, a cyclohexyl group or a cyclohexylmethyl group may be mentioned.

A halogenated monovalent saturated hydrocarbon group in the compound (1) is a group derived from a monovalent saturated hydrocarbon group by replacing at least one of the hydrogen atoms attached to carbon atoms in it by at least one halogen atom.

A halogenated monovalent saturated hydrocarbon group may have a linear, branched, cyclic or partially cyclic structure. The number of carbon atoms in a halogenated monovalent saturated hydrocarbon group is preferably from 1 to 20, in particular from 1 to 10, though there is no particular restriction. A halogenated monovalent saturated hydrocarbon group may be a group derived from a monovalent saturated hydrocarbon group by replacing all the hydrogen atoms attached to carbon atoms by halogen atoms (hereinafter referred to as a perhalogenated monovalent saturated hydrocarbon group) or by replacing some of the hydrogen atoms by halogen atom(s) (hereinafter referred to as a partially halogenated monovalent saturated hydrocarbon group).

In the present specification, "perhalogenated" is prefixed to the name of a group when substantially all the hydrogen atoms attached to carbon atoms in it are replaced by halogen atoms, and "partially halogenated" is prefixed to the name of a group when part of the hydrogen atoms attached to carbon atoms are replaced by halogen atoms. When the halogen atoms can be specified, for example, "perfluoro", "partially fluorinated", "partially chlorinated" or the like is prefixed. The perhalogenated group preferably means a group in which all the hydrogen atoms attached to carbon atoms are replaced by halogen atoms, but includes such a group having some remaining hydrogen atoms provided that it has the same properties as a perhalogenated group.

The halogen atoms in a halogenated monovalent saturated hydrocarbon group are preferably fluorine atoms, chlorine atoms or bromine atoms, particularly preferably fluorine atoms or bromine atoms. The halogenated monovalent saturated hydrocarbon group preferably is a group having fluorine atoms alone as the halogen atoms (hereinafter referred to as a fluoro monovalent saturated hydrocarbon group) or a group having a fluorine atom and at least one other halogen atom (preferably a chlorine atom).

Examples of halogenated monovalent saturated hydrocarbon groups include, for example, a chloromethyl group, a bromomethyl group, a 2,3-dichloropropyl group and a 3,4-dichlorobutyl group.

A hetero atom-containing monovalent saturated hydrocarbon group in the compound (1) is a monovalent saturated hydrocarbon group containing a hetero atom or a hetero atom group. The hetero atom-containing monovalent saturated hydrocarbon group may have a linear, branched, cyclic or partially cyclic structure.

The hetero atom in the hetero atom-containing monovalent saturated hydrocarbon group is preferably a bivalent hetero atom or a bivalent hetero atom group inert to the fluorination. As the bivalent hetero atom inert to the fluorination, an ether oxygen atom, (—O—), may be mentioned, and as the bivalent hetero atom group, for example, —C—C(=O)—C— or —C—SO$_2$—C— may be mentioned. A hetero atom-containing monovalent saturated hydrocarbon group preferably contains an ether oxygen atom, preferably from 1 to 3 ether oxygen atoms.

A hetero atom-containing monovalent saturated hydrocarbon group as $R^A$ or $R^B$ is preferably a linear or branched alkoxyalkyl group having a carbon number of from 1 to 20, preferably from 1 to 10.

A hetero atom-containing monovalent saturated hydrocarbon group as $R^C$ or $R^D$ is preferably a linear or branched alkoxyalkyl group or a linear or branched alkoxy group having a carbon number of from 1 to 20, preferably from 1 to 10, or, in the case of an alkoxy group, from 1 to 8.

As the alkoxy alkyl group, a group derived from a $C_{1-10}$ (preferably $C_{1-2}$) linear or branched alkyl group by replacing one hydrogen atom in it by a linear or branched $C_{1-8}$ alkoxy group may be mentioned. As the alkoxyalkyl group, an ethoxymethyl group, a 1-propoxyethyl group, a 2-propoxyethyl group or the like may be mentioned. As the alkoxy group, a methoxy group, an ethoxy group, a propoxy group or a 2-propoxy group may be mentioned.

A halogenated (hetero atom-containing monovalent saturated hydrocarbon) group in the compound (1) is a group derived from the above-mentioned hetero atom-containing monovalent saturated hydrocarbon group by replacing at least one hydrogen atom attached to a carbon atom by at least one halogen atom. The halogenated group may have a linear, branched, cyclic or partially cyclic structure.

The halogen atom in a halogenated (hetero atom-containing monovalent saturated hydrocarbon) group is preferably a fluorine atom, a chlorine atom or a bromine atom. The halogenated (hetero atom-containing monovalent saturated hydrocarbon) group is preferably a group derived from a hetero atom-containing monovalent saturated hydrocarbon group by replacing part or all of the hydrogen atoms attached to carbon atoms by fluorine atoms (i.e., a fluoro (hetero atom-containing monovalent saturated hydrocarbon) group) or by a fluorine atom and at least one other halogen atom (preferably a chlorine atom).

The halogenated (hetero atom-containing monovalent saturated hydrocarbon) group is preferably a halogenated (ether oxygen-containing monovalent saturated hydrocarbon) group.

A halogenated (hetero atom-containing monovalent saturated hydrocarbon) group as $R^A$ or $R^B$ is preferably a halogenated alkoxyalkyl group, and a halogenated (hetero atom-containing monovalent saturated hydrocarbon) group as $R^C$ or $R^D$ is preferably a halogenated alkoxyalkyl group or a halogenated alkoxy group. The halogenated alkoxyalkyl group is preferably a linear or branched halogenated alkoxyalkyl group having a carbon number of from 1 to 20, preferably from 1 to 10. The halogenated alkoxy group is preferably a linear or branched halogenated alkoxy group having a carbon number of from 1 to 20, preferably from 1 to 10. The halogenated alkoxy moiety in the halogenated alkoxyalkyl group preferably has a carbon number of from 1 to 8, and the halogenated alkoxy group preferably has a carbon number of from 1 to 8.

As the halogenated (hetero atom-containing monovalent saturated hydrocarbon) group, for example, a 1-(3,4-dichlorobutoxy)ethyl group, a 1-(2-bromoethoxy)ethyl group, a 1-(3,4-dichiloro-1,1-dimethylbutoxy)ethyl group may be mentioned.

The combination of $R^A$ and $R^B$ and the combination of $R^C$ and $R^D$ may form bivalent groups, respectively. The bivalent groups are bivalent saturated hydrocarbon groups, halogenated bivalent saturated hydrocarbon groups, hetero atom-containing bivalent saturated hydrocarbon groups or halogenated (hetero atom-containing bivalent saturated hydrocarbon) groups.

As a bivalent saturated hydrocarbon group, a linear alkylene group, a branched alkylene group, a cycloalkylene group or the like may be mentioned.

As a halogenated bivalent saturated hydrocarbon group, a group derived from a bivalent saturated hydrocarbon group by replacing part or all of the hydrogen atoms attached to carbon atoms by fluorine atoms or by a fluorine atom and at least one other halogen atom (preferably a chlorine atom) may be mentioned.

As a hetero atom-containing bivalent saturated hydrocarbon group, a group derived from a bivalent saturated hydrocarbon group by inserting from 1 to 6 (preferably from 1 to 3) ether oxygen atoms in carbon-carbon bonds or at the end may be mentioned.

As a halogenated (hetero atom-containing bivalent saturated hydrocarbon) group, a group derived from a hetero atom-containing bivalent saturated hydrocarbon group by replacing part or all of the hydrogen atoms attached to carbon atoms by fluorine atoms or by a fluorine atom and at least one other halogen atom (preferably a chlorine atom) may be mentioned.

As a bivalent group, a linear or branched alkylene group or a linear or branched perhalogenated alkylene group is preferred. As the alkylene group, a $C_{2-6}$ linear alkylene group, a branched alkylene group derived from $C_{2-6}$ linear alkylene group by replacing at least one hydrogen atom by a $C_{1-6}$ linear alkyl group is preferred. As a perhalogenated alkylene group, a perfluoroalkylene group is preferred, and a $C_{2-6}$ linear perfluoroalkylene group or a branched perfluoroalkylene group derived from such a perfluoroalkylene group by replacing at least one fluorine atom by a $C_{1-6}$ linear perfluoroalkyl group is particularly preferred.

$X^1$ to $X^6$ in the compound (1) may be the same or different, and each of them means a hydrogen atom or a fluorine atom. In the present invention, it is preferred that all of $X^1$ to $X^3$ are hydrogen atoms. In the compound (1), at least one of $R^A$ to $R^D$ and $X^1$ to $X^6$ is a fluorine-containing group or a fluorine atom.

The groups in the compound (1) have to be selected so that the fluorine content of the compound (1) is 30 mass % or above. The fluorine content is a measurement defined as the ratio (mass %) of the total mass of the fluorine atoms in the compound to the molecular weight of the compound.

The compound (1) has to have a fluorine content not lower than a specific level for the following reason. Fluorination of a compound (1) having an ether oxygen atom by the most common fluorination method, the ECF method, gives a low yield of a fluorinated product due to the cleavage of the C—O bond in the molecule. Fluorination accompanied by a C—O bond cleavage gives a problematic product which is difficult to separate from the desired product, causing the problem of poor purity of the fluorinated product. Liquid phase fluorination of such an ether oxygen-containing compound (1) gives better results than the ECF method, but is insufficient in terms of the yield of the fluorinated product and can be a heterogeneous reaction with poor volume efficiency when the solubility of the compound (1) in the liquid phase is poor.

Therefore, the present inventors tried the process of the present invention which uses an ether oxygen-containing compounds which partially have the same carbon skeleton as the desired compound and have a fluorine content of 30 mass % or above as the substrate in reaction with fluorine in a liquid phase, and as a result, have found out that fluorinated products are obtained in high yield with sufficiently suppressing possible dissociation of the compounds during the fluorination. Then, it has been found out that fluorination of the compound (1) as the substrate gives a high yield of the corresponding fluorinated product, which gives a fluorine-containing acyl fluoride extremely useful as an intermediate of fluorine-containing compounds upon dissociation of the ester group in it.

In the present invention, the fluorine content of the compound (1) is preferably from 30 to 70 mass %. A compound (1) with a fluorine content lower than 30 mass % can not undergo the above-mentioned high yield fluorination and is unlikely to be sufficiently soluble in the liquid phase used for the fluorination. Compounds (1) with excessively high fluorine contents are economically disadvantageous, and their availability is limited.

The molecular weight of the compound (1) is preferably from 200 to 1000. A compound (1) having a molecular weight less than 200 has such a low boiling point that the compound (1) tends to vaporize in the course of fluorination or undergo undesirable dissociation in the liquid phase to give a low yield of the fluorinated product. On the other hand, if the molecular weight exceeds 1000, the solubility in the liquid phase tends to be low.

In the compound (1) of the present invention, the moiety —C($OR^A$)($OR^B$)($CX^1X^2X^3$) is preferably a hydrogen-containing group, and the moiety —$CR^CR^D$($CX^4X^5X^6$) is a fluorine-containing group. $R^C$, $R^D$ or the bivalent group formed from the combination of $R^B$ and $R^D$ is preferably a fluorine-containing group containing no hydrogen atoms in the case of the after-mentioned continuous process.

Further, it is particularly preferred that each of $R^C$ and $R^D$ is a perfluoroalkyl group or a perfluoroalkoxy group, or the combination of $R^C$ and $R^D$ forms a perfluoroalkylene group or a perfluoro($\alpha,\omega$-dioxaalkylene) group. Particularly preferred as such a compound (1) is a compound (8), which will be described later, because it facilitates a continuous process and saves the trouble of separating the product.

In the fluorination step, the compound (1) reacts with fluorine in a liquid phase to give a compound (2). The step involves so-called liquid phase fluorination. Fluorine is preferably supplied alone in the form of fluorine gas or with an inert gas as a diluent to the liquid phase. As an inert gas, nitrogen gas or helium gas is preferred. Nitrogen gas is particularly preferred from an economical aspect. When fluorine gas diluted with an inert gas is used, the amount of fluorine gas in relation to nitrogen gas is preferably at least 10 vol %, in particular at least 20 vol %, in terms of efficiency, though there is no particular restriction.

The liquid phase of choice is preferably a solvent which is inert to fluorine and dissolves the compound (1) (hereinafter referred to as a solvent I). The solvent I is preferably a solvent which contains no C—H bonds but necessarily contains a C—F bond, in particular an organic solvent consisting of a compound derived from a known organic solvent having at least one atom selected from the group consisting of chlorine atoms, nitrogen atoms and oxygen atoms in the structure by replacing all the hydrogen atoms by fluorine. As the solvent (I), a solvent in which the solubility of the compound (1) is high, in particular at least 1 mass % (preferably at least 5 mass %), is preferably used.

As the solvent I, the compound (2), the fluorinated acyl fluoride (3), the compound (6), which will be described later, perfluoropolyethers (trade names: KRYTOX, FOMBLIN, GALDEN and Demnum), chlorofluorocarbons (trade names: Flon Lube), perfluoroalkylamines (such as perfluorotrialkylamines), an inert fluid (trade name: Fluorinert) are preferred. Particularly preferred are perfluorotrialkylamines, the compound (6) (wherein $R^C$ and $R^D$ are the same or different perfluorinated groups, and $X^4$, $X^5$, $X^6$ and Y are all fluorine atoms) or the fluorinated acyl fluoride (3). The amount of the solvent I is preferably at least five times, in particular from 10 to 100 times, by mass as large as that of the compound (1).

As to the mode of fluorination, in the present invention, the fluorination is preferably carried out batchwise or continuously. Especially, the fluorination method 2, which will be described below, is preferred from the viewpoint of reaction yield and selectivity. Whether the fluorination is batchwise or continuous, fluorine gas diluted with an inert gas such as nitrogen gas may be used.

[Fluorination method 1] A method comprising loading a reactor with the compound (1) and the solvent I, starting stirring, adjusting the reactor to given reaction temperature and reaction pressure, and then carrying out the reaction while continuously supplying fluorine gas optionally with the solvent I.

[Fluorination method 2] A method comprising loading a reactor with the solvent I, starting stirring, adjusting the reactor to given reaction temperature and reaction pressure, and then continuously supplying fluorine gas and the compound (1) in a given molar ratio.

In the fluorination method 2, the compound (1) is preferably supplied in the form of solution in the solvent I to improve selectivity and reduce by-products. It is preferred to dissolve the compound (1) in at least five times, preferably at least 10 times, by mass as much of the solvent I.

As to the amount of fluorine used for the fluorination, batchwise or continuous, it is preferred to constantly secure an excess of fluorine in terms of equivalent weights over the hydrogen atoms in the compound (1) in view of selectivity. The amount of fluorine ($F_2$) is preferably at least 1.1 times as many equivalent weights (i.e., at least 1.1 times as many moles), in particular at least 1.5 times as many equivalent weights (i.e., at least 1.5 times as many moles). Because it is preferred to always secure an excess of fluorine during the reaction from beginning to end, it is preferred to preliminarily dissolve fluorine in the solvent I to be loaded into the reactor.

The reaction temperature during the fluorination is preferably between −60° C. and the boiling point of the compound (1). In general, it is preferably between −50° C. and +100° C., in particular between −20° C. and room temperature (about 25° C.), in view of yield, selectivity and ease of industrial operations. The reaction pressure during the fluorination is particularly preferably 0–2 MPa (gauge pressure) in view of yield, selectivity and ease of industrial operations.

Addition of a C—H bond-containing compound to the reaction system, long retention of the compound (1) in the reaction system, irradiation with ultraviolet light and the like are preferred to promote fluorination efficiently. These operations are preferably carried out at the later period of the fluorination. These operations increase the efficiency of the fluorination of the compound (1) in the reaction system and drastically improve the degree of conversion. In the case of irradiation with ultraviolet light, the irradiation time is preferably from 0.1 to 3 hours.

The C—H bond-containing compound is selected from organic compounds other than the compound (1), and an aromatic hydrocarbon is preferable. Particularly preferred is, for example, benzene or toluene. The amount of a C—H bond-containing compound is preferably from 0.1 to 5 mol % in relation to the compound (1). Such a C—H bond-containing compound is preferably added in the presence of fluorine gas in the reaction system. When a C—H bond-containing compound is added, it is preferred to apply pressure to the reaction system (preferably to 0.01 to 5 MPa (gauge pressure)).

The compound (1) is converted to the compound (2) in the fluorination step. In the fluorination step, fluorine atoms replace hydrogen atoms attached to carbon atoms but do not replace chlorine atoms, bromine atoms or iodine atoms attached to carbon atoms. It follows that when $R^C$ and $R^D$ in the compound (1) are hydrogen atoms, $R^{CF}$ and $R^{DF}$ are fluorine atoms, and that when $R^C$ and $R^D$ are halogen atoms, $R^{CF}$ and $R^{DF}$ are the same as $R^C$ and $R^D$, respectively.

Monovalent groups as $R^{AF}$, $R^{BF}$, $R^{CF}$ and $R^{DF}$ in the compound (2) are preferably linear or branched perfluoroalkyl groups or linear or branched perfluoroalkoxyalkyl groups having a carbon number of from 1 to 20, particularly preferably from 1 to 10.

In the compound (2), $R^{AF}$ and $R^{BF}$, or $R^{CF}$ and $R^{DF}$, may form a bivalent group. A bivalent group formed from $R^{AF}$ and $R^{BF}$, or $R^{CF}$ and $R^{DF}$, is a fluorinated derivative of a bivalent group formed from the combination of $R^A$ and $R^B$, or the combination of $R^C$ and $R^D$ provided that when the bivalent group contains no hydrogen atom attached to a carbon atom, the bivalent group formed from the combination of $R^{AF}$ and $R^{BF}$, or the combination of $R^{CF}$ and $R^{DF}$ the same as the is the same as the bivalent group formed from the combination of $R^A$ and $R^B$, or the combination of $R^C$ and $R^D$.

Bivalent groups formed from the combination of $R^{AF}$ and $R^{BF}$, or the combination of $R^{CF}$ and $R^{DF}$, are, for example, perfluoro bivalent saturated hydrocarbon groups, perfluoro (halogenated bivalent saturated hydrocarbon) groups, perfluoro(hetero atom-containing bivalent saturated hydrocarbon) groups or perfluoro(halogenated (hetero atom-containing) bivalent saturated hydrocarbon)) groups. Among them, perfluoroalkylene groups and perfluoro(α,ω-dioxaalkylene) groups are preferable. Particularly preferred as such a compound (2) is a compound (9), which will be described later, because it facilitates a continuous process, which will be described later, and saves the trouble of separating the product.

In the present invention, the fluorination step is followed by a step of dissociating the ester bond in the compound (2) to give a fluorinated acyl fluoride (3) (hereinafter referred to as an ester dissociation step).

The ester dissociation step may be carried out by heating the compound (2) to dissociate the ester bond (hereinafter referred to as the pyrolysis method) or by reacting the compound (2) with an electrophile or a nucleophile in a liquid phase, without any particular restriction. In the case of the pyrolysis method, selections of conditions preferably includes consideration of the boiling point of the compound (2) and safety.

For example, when the compound (2) is volatile, gas phase pyrolysis is preferably used by dissociating the compound (2) continuously in a gas phase and condensing and collecting the resulting fluorinated acyl fluoride (3) from the gas. The heating temperature during the gas phase pyrolysis is preferably from 50 to 350° C., particularly from 50 to 300° C., particularly preferably from 150 to 250° C. In the gas phase pyrolysis, an inert gas which does not participate in the reaction may be added to promote vaporization of the compound (2). As the inert gas, nitrogen, carbon dioxide, oxygen or the like may be mentioned. An inert gas is preferably added in an amount of from 0.01 to 50 vol % of the compound (2). If the amount of an inert gas is less than 0.01 vol %, the addition of the inert gas is likely to have little effect, and if the amount of an inert gas is more than 50 vol %, the recovery of the dissociation product can be low.

Meanwhile, if the compound (2) is nonvolatile, liquid phase pyrolysis is preferably used by heating the compound (2) in a liquid state in a reactor. The heating temperature during the liquid phase pyrolysis is preferably from 50 to 300° C., particularly preferably from 100 to 250° C. The reaction pressure is not particularly restricted. In the liquid phase pyrolysis, the reaction is preferably accompanied by distillation by using a reactor equipped with a distillation column because the resulting fluorinated acyl fluoride (3) usually has a lower boiling point than the compound (2). The fluorinated acyl fluoride (3) produced can be withdrawn from the reaction system continuously by distillation. The product may be withdrawn from the reactor at once after completion of heating.

The liquid phase pyrolysis may be carried out by heating the compound (2) alone (i.e., in the absence of a solvent) or by heating the compound (2) in the presence of a solvent (hereinafter referred to as a solvent II). The solvent II is not particularly restricted so long as it is unreactive and compatible with the compound (2) and is unreactive with the resulting fluorinated acyl fluoride (3). The solvent II of choice is preferably a solvent which is easily separated by purification of the fluorinated acyl fluoride (3). Preferable examples of the solvent II include inert solvents such as perfluorotrialkylamines and perfluoronaphthalene and high-boiling chlorofluorocarbons called chlorotrifluoroethylene oligomers (such as the one sold under the trade name: Flon Lube). The amount of the solvent II to be used is preferably from 10 to 1000 mass % in relation to the compound (2).

When the ester bond is dissociated through reaction with a nucleophile or electrophile in a liquid phase, the reaction may be carried out in the absence of a solvent or in the presence of a solvent (hereinafter referred to as a solvent III), preferably in the absence of a solvent. As the solvent III, solvents mentioned for the solvent II are preferable. The nucleophile is preferably a fluoride ion (F$^-$), particularly preferably a fluoride ion derived from an alkali metal fluoride. The alkali metal fluoride is preferably NaF, NaHF$_2$, KF or CsF. Among them, NaF is particularly preferred from an economical aspect, and KF is particularly preferred in view of reactivity.

When a nucleophile (such as F$^-$) is used, F$^-$ is supposed to attach to the carbonyl group in the ester bond in the compound (2) nucleophilically to give (R$^{AF}$O)(R$^{BF}$O)C(CF$_3$)CF$_2$O$^-$ and a compound (4), which will be described later. Then, (R$^{AF}$O) (R$^{BF}$O)C(CF$_3$)CF$_2$O$^-$ detaches the F$^-$ ion to give a fluorinated acyl fluoride (3). The detached F$^-$ is supposed to act as a nucleophile again on another molecule of the compound (2) to react the same way.

When a nucleophile is used, though its minimum initial amount is a catalytic amount, it may be used excessively. The amount of a nucleophile is preferably from 1 to 500 mol %, particularly preferably from 10 to 100 mol %, extremely preferably from 5 to 50 mol %, in relation to the compound (2). When a nucleophile is used, the lower limit of the reaction temperature is preferably −30° C. or above, and the upper limit is preferably the boiling point of the solvent III or the compound (2), whichever is lower. It is usually from −20° C. to 250° C. The reaction is also preferably carried out in a reactor equipped with a distillation column. The use of NaF as the nucleophile prevents the compound from dissociation and thereby facilitates the pyrolysis at low temperature. Therefore, in the present invention, it is particularly preferred to dissociate the ester bond in the presence of NaF.

The ester dissociation step yields a fluorinated acyl fluoride (3). R$^{AF}$ and R$^{BF}$ in the formula (3) are defined as the same as in the compound (2). The ester dissociation step yields not only the fluorinated acyl fluoride (3) but also the following compound (4). The compound (4) has such a boiling point that it can be recovered, and its recovery increases the efficiency of the process. In this case, the reaction scheme is represented by the following chemical formula using the compounds (1) to (4) wherein R$^{CF}$ and R$^{DF}$ are the same as defined above.

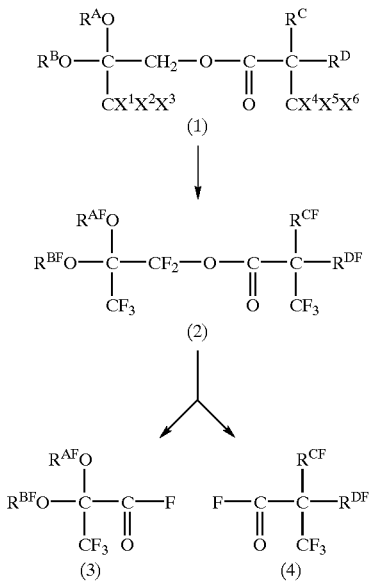

In the above scheme, the ester bond —CF$_2$—O—CO— in the compound (2) splits into two —COF groups. Thus, dissociation of the compound (2) gives the fluorinated acyl fluoride (3) and the compound (4). The ester dissociation step in the present invention necessarily gives the fluorinated acyl fluoride (3) but may give both the fluorinated acyl fluoride (3) and the compound (4).

In the present invention, as the compound (2), a compound (9) which is a compound (2) wherein R$^{CF}$ is the same as OR$^{AF}$, and R$^{DF}$ is the same as OR$^{BF}$, is preferably used.

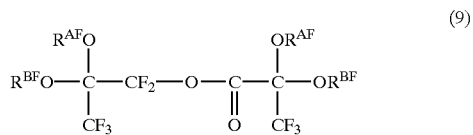

The use of a compound (9) as the compound (2) means that dissociation of one molecule of the compound (2) theoretically gives two molecules of the fluorinated acyl fluoride (3), as is evident from the above reaction scheme, and therefore, increases the yield of the fluorinated acyl fluoride (3), if the fluorinated acyl fluoride (3) only is desired. In addition, the use of the compound (9) has the advantage of obviating the step of separating the other product resulting from the dissociation of the ester bond.

Furthermore, when the compound (2) is a compound (9), the use of part or all of the resulting fluorinated acyl fluoride (3) as a compound (6) permits continuous production of the fluorinated acyl fluoride (3).

The compound (1) in the present invention is preferably obtained by reacting a compound (5) and a compound (6) (hereinafter the reaction step is referred to as the esterification step), wherein R$^A$, R$^B$, R$^C$, R$^D$, X$^1$, X$^2$, X$^3$, X$^4$, X$^5$ and X$^6$ are the same as defined above, and Y is a halogen atom.

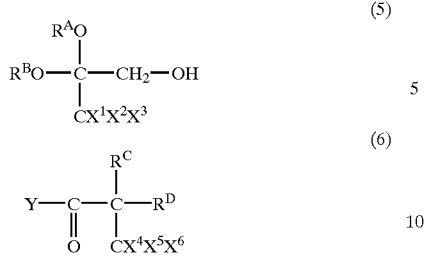

(5)

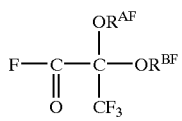

(7)

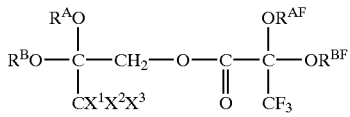

(8)

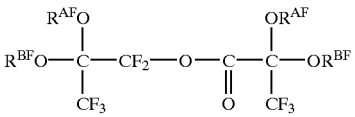

(9)

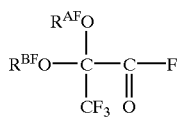

(3)

(6)

The compound (5) is readily available or can be readily synthesized by known methods, for example, by following the syntheses of 2-alkoxyalcohols disclosed in J. Am. Chem. Soc., 49, 1080 (1927), Bull. Soc. Chim. Fr., 1813 (1960), Can. J. Chem., 43, 1030 (1965) and Synthesis, 280 (1981). The compound (6) is readily available or can be readily synthesized by known methods.

Y in the compound (6) is a halogen atom, preferably a chlorine atom or a fluorine atom. Especially, when the fluorinated acyl fluoride (3) obtained in the esterification step is used as the compound (6), Y is a fluorine atom.

The reaction in the esterification step may be carried out in the presence of a solvent (hereinafter referred to as a solvent IV) but preferably carried out in the absence of the solvent IV in view of volume efficiency. The solvent IV, if used, is preferably dichloromethane, chloroform, triethylamine or a solvent mixture of triethylamine with tetrahydrofuran. The solvent IV is preferably used in an amount of from 50 to 500 mass %, in relation to the total amount of the compound (5) and the compound (6).

The reaction in the esterification step gives an acid represented by HY. When the compound (6) is a HF-generating compound having a fluorine atom as Y, an alkali metal fluoride (such as NaF) or a trialkylamine may be added to the reaction system as a HF scavenger. A HF scavenger is preferably used when the compound (5) or the compound (6) is acid instable. When no HF scavenger is used, it is preferred to exhaust HF with a nitrogen stream from the reaction system. The amount of an alkali metal fluoride is preferably from 1 to 10 times as many moles as that of the compound (6).

The reaction temperature during the esterification step is usually preferably −50° C. or above, particularly preferably a temperature between −50° C. and 100° C. or between −50° C. and the boiling point of the solvent. The reaction time during the esterification step can be varied in accordance with the feed rate of the starting materials and the amounts of the reactants. The reaction pressure is preferably from 0 to 2 MPa (gauge pressure).

The process for preparing a fluorinated acyl fluoride (3) of the present invention preferably comprises reacting a compound (5) with a compound (7) to form a compound (8) having a fluorine content of 30 mass % or above, fluorinating the compound (8) in a liquid phase to form a compound (9) and dissociating the ester bond in the compound (9), wherein $R^A$, $R^B$, $X^1$, $X^2$, $X^3$, $R^{AF}$ and $R^{BF}$ are the same as defined above.

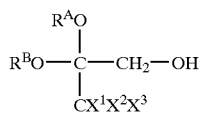

(5)

Preferable examples of $R^A$, $R^B$, $X^1$, $X^2$, $X^3$, $R^{AF}$ and $R^{BF}$ are the same as mentioned previously. Especially, hetero atom-containing monovalent saturated hydrocarbon groups as $R^A$ and $R^B$ are preferably ether oxygen-containing monovalent saturated hydrocarbon groups, and halogenated (hetero atom-containing monovalent saturated hydrocarbon) groups as $R^A$ and $R^B$ are preferably halogenated (ether oxygen-containing monovalent saturated hydrocarbon) groups. Further, it is preferred that $X^1$, $X^2$ and $X^3$ are all hydrogen atoms.

Further, $R^A$ and $R^B$ are preferably linear or branched alkyl groups or linear or branched alkoxyalkyl groups having a carbon number of from 1 to 20, preferably from 1 to 10. $R^{AF}$ and $R^{BF}$ are preferably linear or branched perfluoroalkyl groups or linear or branched perfluoroalkoxyalkyl groups having a carbon number of from 1 to 20, preferably from 1 to 10.

Further, in the present invention, the fluorine content of the compound (8) is preferably from 30 to 70 mass %. A compound (8) with a fluorine content lower than 30 mass % can not undergo the above-mentioned high yield fluorination as described previously. Compounds (8) with excessively high fluorine contents may be hardly available and economically disadvantageous.

The molecular weight of the compound (8) is preferably from 200 to 1000. A compound (8) having a molecular weight less than 200 tends to vaporize in the course of fluorination causing gas phase reaction and therefore tends to result in a lower yield of the fluorinated products. On the other hand, if the molecular weight exceeds 1000, the solubility in the liquid phase tends to be low.

In the present invention, part of the fluorinated acyl fluoride (3) resulting from the dissociation of the compound (9) is preferably used as at least part of the compound (7) to be reacted with the compound (5) to continuously produce the fluorinated acyl fluoride (3). The reaction scheme in the continuous process is represented by the following formula.

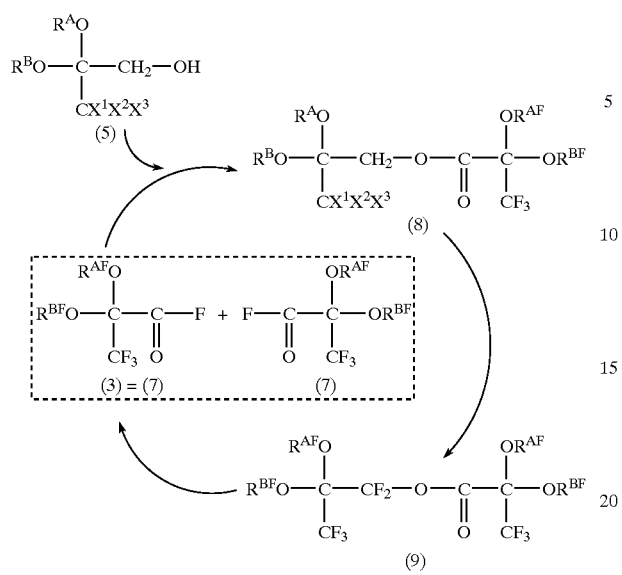

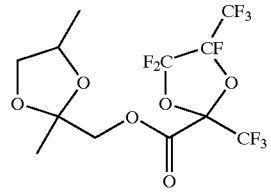

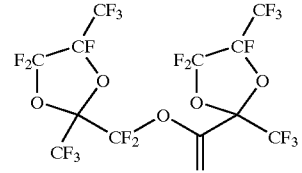

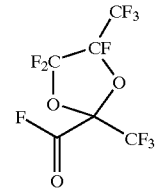

As shown in the above reaction scheme, the fluorinated acyl fluoride (3) resulting from the dissociation of the compound (9) has the same chemical structure as the compound (7) to be reacted with the compound (5). Because the dissociation of the compound (9) theoretically yields two molecules of the fluorinated acyl fluoride (3), separation of the product is not necessary. After as much of the fluorinated acyl fluoride (3) as needed is collected, the rest of the fluorinated acyl fluoride (3) is used as the compound (7) for continuous production of the fluorinated acyl fluoride (3).

The reuse of one of the two molecules of the fluorinated acyl fluoride (3) resulting from the compound (9) permits continuous synthesis of the fluorinated acyl fluoride (3) without fresh feed of the compound (7) stoichiometrically.

Example of the process for preparing a fluorinated acyl fluoride (3) of the present invention are given below.

The first example is a process for preparing the following compound (15), which comprises reacting the following compound (13) with the following compound (14) to form the compound (11) having a fluorine content of 30 mass% or above, then reacting the compound (11) with fluorine in a liquid phase to form the following compound (12), and dissociating the ester bond in the compound (12) wherein Y is the same as defined previously.

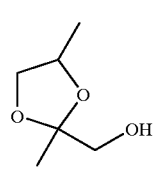

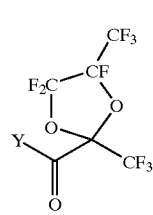

In the above example, when Y in the compound (14) is a fluorine atom, it is possible to obtain the compound (15) continuously in accordance with the following reaction scheme.

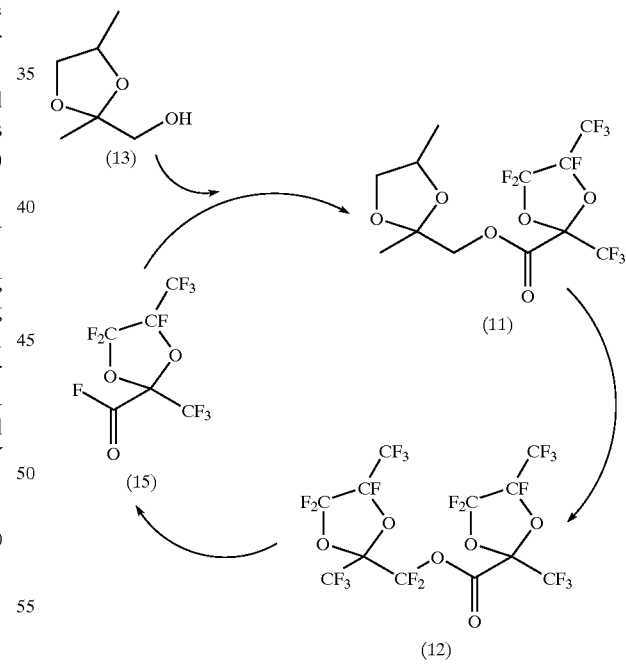

The second example is a process for preparing the following compound (20), which comprises reacting the following compound (16) with the following compound (17) to form the following compound (18) having a fluorine content of 30 mass % or above, then reacting the compound (18) with fluorine in a liquid phase to form the following compound (19), and dissociating the ester bond in the compound (19) wherein Y is the same as defined previously:

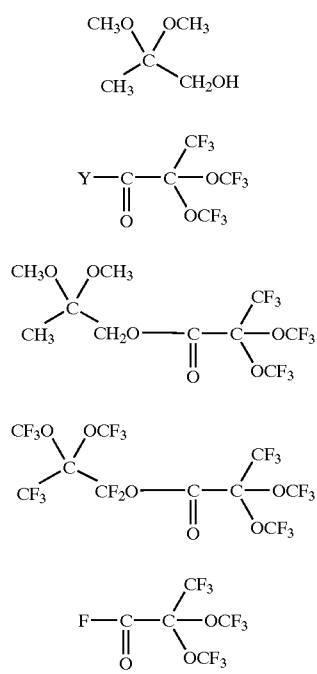

(16)
(17)
(18)
(19)
(20)

The third example is a process for preparing the following compound (25), which comprises reacting the following compound (21) with the following compound (22) to form a compound represented by the following compound (23) having a fluorine content of 30 mass % or above, then reacting the compound (23) with fluorine in a liquid phase to form the following compound (24), and dissociating the ester bond in the compound (24) wherein Y is the same as defined previously.

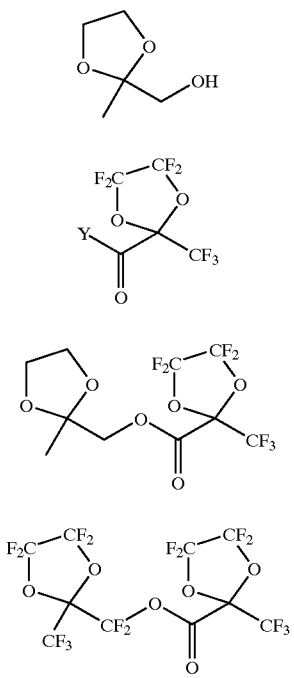

(21)
(22)
(23)
(24)

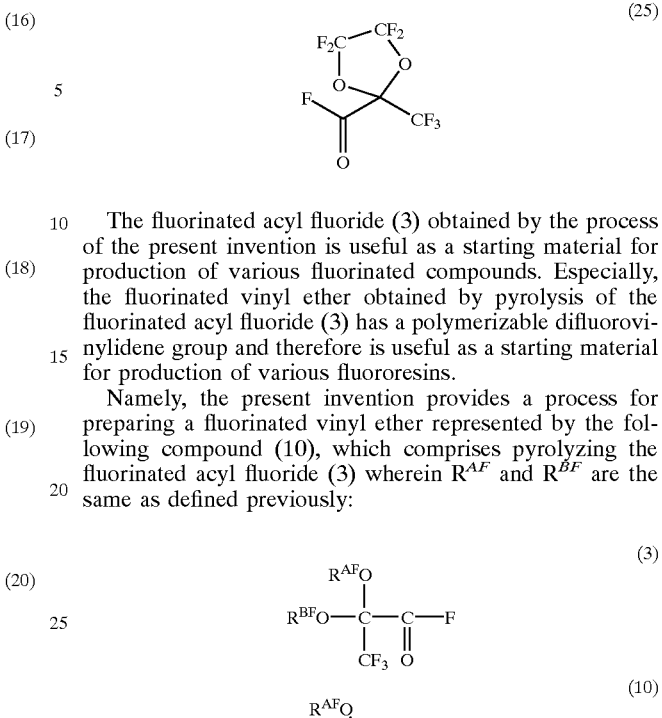

(25)

The fluorinated acyl fluoride (3) obtained by the process of the present invention is useful as a starting material for production of various fluorinated compounds. Especially, the fluorinated vinyl ether obtained by pyrolysis of the fluorinated acyl fluoride (3) has a polymerizable difluorovinylidene group and therefore is useful as a starting material for production of various fluororesins.

Namely, the present invention provides a process for preparing a fluorinated vinyl ether represented by the following compound (10), which comprises pyrolyzing the fluorinated acyl fluoride (3) wherein $R^{AF}$ and $R^{BF}$ are the same as defined previously:

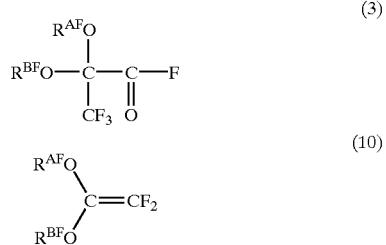

(3)

(10)

The fluorinated acyl fluoride (3) may be pyrolyzed by any method without any particular restriction, for example, by gas phase pyrolysis of the fluorinated acyl fluoride (3) or by pyrolysis of an alkali carboxylate resulting from the reaction of the fluorinated acyl fluoride (3) with an alkali hydroxide.

The reaction temperature during the gas phase pyrolysis of the fluorinated acyl fluoride (3) is preferably from 250 to 400° C., particularly preferably from 250 to 350° C. The reaction temperature during the above-mentioned pyrolysis of an alkali carboxylate is preferably from 150 to 350° C., particularly preferably from 200 to 280° C. If the reaction temperature during the gas phase pyrolysis is lower than 250° C. or the reaction temperature during the pyrolysis of an alkali carboxylate is lower than 150° C., the conversion to the compound (10) tends to be low. If the reaction temperature during the gas phase pyrolysis is higher than 400° C. or the reaction temperature during the pyrolysis of the alkali carboxylate is higher than 350° C., the fluorinated acyl fluoride (3) is unlikely to be pyrolyzed into the compound (10) in favor of a different pyrolysate.

The gas phase pyrolysis of the fluorinated acyl fluoride (3) is preferably carried out continuously by introducing vapor of the fluorinated acyl fluoride (3) into a hot reaction tube and collecting the resulting unsaturated compound (10) continuously by condensing the outlet gas. For the gas phase pyrolysis, a tubular reactor is preferably used. The retention time in a tubular reactor is preferably about from 0.1 second to 10 minutes on an empty basis. The reaction pressure is not particularly restricted. When the fluorinated acyl fluoride (3) is a high-boiling compound, the reaction is carried out preferably under reduced pressure. Especially, when the fluorinated acyl fluoride (3) is a low-boiling compound, the reaction is preferably carried out under pressure to suppress the dissociation of the product and increase the reactivity.

In the gas phase pyrolysis in a tubular reactor, it is preferred to pack the reaction tube with glass, an alkali metal salt or an alkaline earth metal salt to promote the reaction. As the alkali metal salt or alkaline earth metal salt, a carbonate or a fluoride is preferred. As the glass, common soda glass, especially in the form of fluidizable glass beads, is preferred. As the alkali metal salt, sodium carbonate, sodium fluoride, potassium carbonate or lithium carbonate may be mentioned. As the alkaline earth metal salt, calcium carbonate, calcium fluoride or magnesium carbonate may be mentioned. Further, when the reaction tube is packed with glass, an alkali metal salt or an alkaline earth metal salt, glass beads or sodium carbonate known as light ash having particle sizes of about from 100 to 250 μm is preferably used to carry out the reaction in a fluidized bed.

In the gas phase pyrolysis, the reaction is preferably carried out in the presence of an inert gas which does not directly participate in the pyrolysis to promote the vaporization of the fluorinated acyl fluoride (3). As the inert gas, nitrogen, carbon dioxide, helium, argon or the like is mentioned. The amount of an inert gas is preferably about from 0.01 to 50 vol % of the fluorinated acyl fluoride (3). Too much of an inert gas can unfavorably lower the recovery of the product. On the other hand, if the fluorinated acyl fluoride (3) has a high boiling point, the pyrolysis may be carried out in a liquid phase.

Examples of the above-mentioned process for preparing a fluorinated vinyl ether are given below.

The first example is a process for preparing a fluorinated vinyl ether, which comprises pyrolyzing the compound (15) obtained by the previously mentioned process to form the following compound (26).

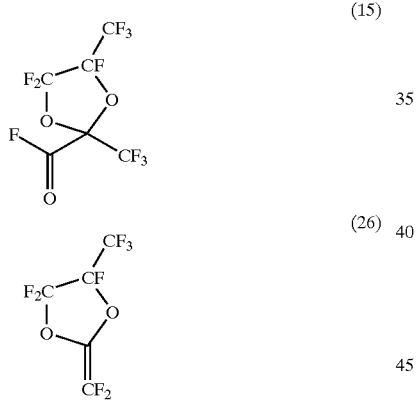

(15)

(26)

The second example is a process for preparing a fluorinated vinyl ether, which comprises pyrolyzing the compound (20) obtained by the previously mentioned process to form the following compound (27).

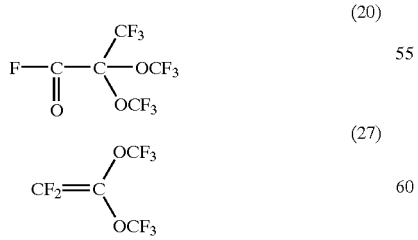

(20)

(27)

The third example is a process for preparing a fluorinated vinyl ether, which comprises pyrolyzing the compound (25) obtained by the previously mentioned process to form the following compound (28).

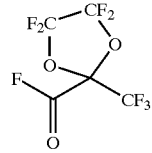

(25)

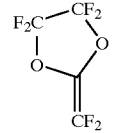

(28)

The compound (10), the compound (26), the compound (27) and the compound (28) are fluorine compounds having a polymerizable double bond in the molecule and is both homopolymerizable and copolymerizable with other compounds having an unsaturated bond. Therefore, they are highly useful as monomers for synthesis of various fluororesins.

The following compound (11) and the following compound (12) are novel chemical substances. These compounds are also highly useful as precursors of the compound (26) which is a useful monomer for synthesis of fluororesins.

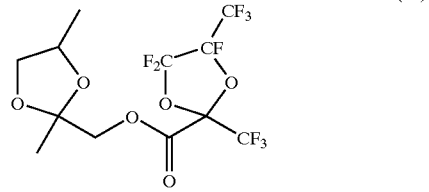

(11)

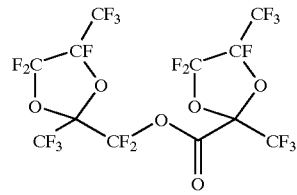

(12)

EXAMPLES

Now, the present invention will be described in further detail with reference to preferable Examples, but the present invention is not limited thereto. Hereinafter, gas chromatography is referred to as GC, gas chromatography mass spectrometry is referred to as GC-MS, tetramethylsilane as TMS, and 1,1,2-trichlorotrifluoroethane as R-113. The NMR spectra data are shown as apparent ranges of chemical shifts. In $^{13}$C-NMR, CDCl$_3$ was used as the standard substance and gave the standard value 76.9 ppm. The purity determined from the GC peak areas is referred to as the GC purity. The yield determined from the peak areas in the NMR spectrum is referred to as the NMR yield.

Example 1

Example 1-1

Esterification Step

The following compound (13) (15.0 g, GC purity 98%), triethylamine (12.7 g) and dichloropentafluoropropane (25.1 g, AK-225 manufactured by Asahi Glass Co., Ltd.) were stirred in a flask on an ice bath. The following compound (15) (38.8 g) was added dropwise thereto over 1 hour while the internal temperature was kept at 10° C. or below. After the dropwise addition, the mixture was stirred at room temperature for 2 hours and combined with ice-cold water (100 mL). The resulting crude liquid was partitioned, and the lower layer was withdrawn. The lower layer withdrawn was washed with water (50 mL) twice, dried over magnesium sulfate and filtered to give a crude liquid. Vacuum distillation of the crude liquid gave 26.4 g of the following compound (11) in a fraction distilled at 75–77° C./1.3 kPa (absolute pressure). The compound (11) had a 99% purity and a fluorine content of 40.5 mass %. The data obtained from the NMR spectra of the compound (11) are as follows.

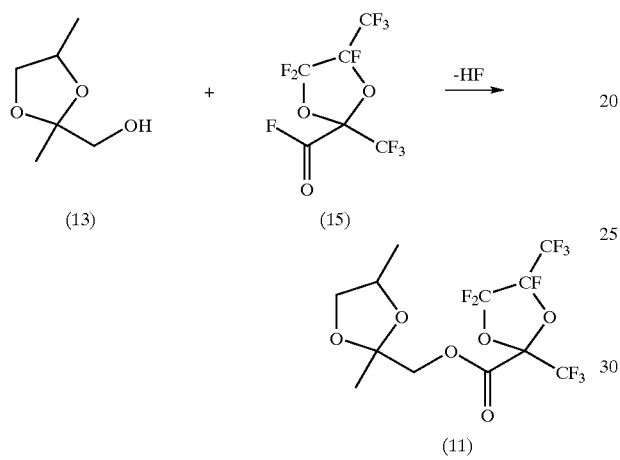

$^1$H-NMR(300.4 MHz, solvent:CDCl$_3$, standard:CHCl$_3$) δ(ppm):1.26~1.29(m, 3H), 1.38, 1.39, 1.42, 1.43(s, 3H), 3.40~3.51(m, 1H), 4.00~4.11(m, 1H), 4.20~4.40(m, 3H).

$^{19}$F-NMR (282.7 MHz, solvent:CDCl$_3$, standard:CFCl$_3$) δ(ppm): −77.7~−78.5(1F), −80.2~−80.3(3F), −80.8~−81.0(3 F), −82.6~−83.9(1F), −123.5~−123.9(m, 1F).

Example 1-2

Fluorination Step

R-113 (311 g) was put in a 500 cc nickel autoclave and stirred at 25° C. To the gas outlet of the autoclave, a cooler maintained at 20° C., a filler bed of Naf pellets and a cooler maintained at −10° C. were connected in series. A liquid return line was provided to return the condensate from the cooler maintained at −10° C. to the autoclave. After nitrogen gas was introduced for 1.0 hour, fluorine gas diluted to 20 vol % with nitrogen gas (hereinafter referred to diluted fluorine gas) was introduced at a flow rate of 8.35 L/h for 1 hour. Then, while the diluted fluorine gas was introduced at the same flow rate, the compound (11) (5.00 g) obtained in the esterification step dissolved in R-113 (100 g) was injected over 3.5 hours.

Then, while the diluted fluorine gas was introduced at the same flow rate, 9 mL of 0.01 g/mL benzene solution in R-113 was injected with a temperature rise from 25° C. to 40° C. The benzene inlet of the autoclave was closed, and then the outlet valve of the autoclave was closed. When the pressure reached 0.20 MPa (gauge pressure), the fluorine gas inlet valve of the autoclave was closed, and stirring was continued for 0.6 hour. Then, the pressure was returned to ordinary pressure, and while the temperature inside the reactor was maintained at 40° C., 6 mL of the same benzene solution was injected, and the benzene inlet of the autoclave and then the outlet valve of the autoclave were closed. When the pressure reached 0.20 MPa (gauge pressure), the fluorine gas inlet valve of the autoclave was closed, and stirring was continued for 0.5 hour. The same procedure was repeated once more. Benzene was injected in a total amount of 0.217 g, and R-113 was injected in a total amount of 21 mL. Nitrogen gas was introduced for another 1 hour. Quantitative analysis by $^{19}$F-NMR (internal standard: C$_6$F$_6$) revealed that the yield of the resulting compound was 73.8%, gave the following NMR spectrum data which demonstrate formation of the following compound (12).

$^{19}$F-NMR(376.0 MHZ, solvent:CDCl$_3$, standard:CFCl$_3$) δ(ppm): −77.6~−80.2(2F), −80.0~−81.7(13F), −83.4~−87.2(3 F), −123.0~−126.0(2F).

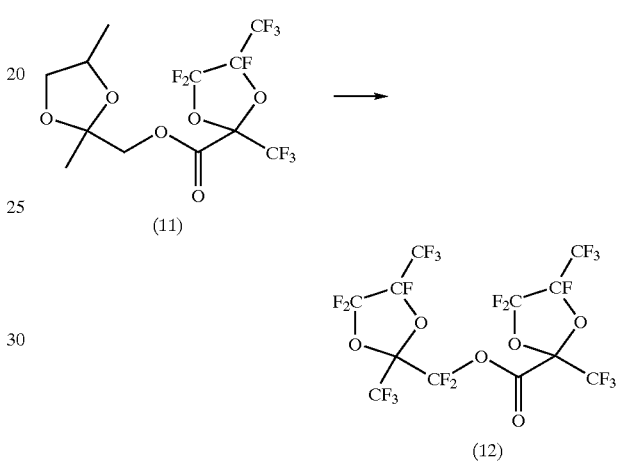

Example 1-3

Ester Dissociation Step

The compound (12) (2.1 g) obtained in the fluorination step was loaded into a flask together with NaF powder (0.02 g) and heated at 120° C. on an oil bath with vigorous stirring for 10 hours, with a reflux condenser adjusted to a temperature of 20° C. above the flask. After cooling, the liquid sample (2.0 g) was recovered. GC-MS analysis of the sample identified the following compound (15) as the main component. The yield of the compound (15) was 71.2%.

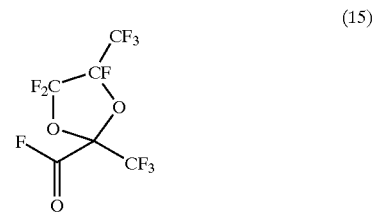

Example 1-4

Example of Preparation of Fluorinated Vinyl Ether by Pyrolysis

As a preheater, a 6 m-long SUS316 preheater with an inner diameter of 3 mm was used, as a fluidized bed, a 150 mm-long SUS316 fluidized bed with an inner diameter of 9.2 mm packed with sufficiently dried K$_2$CO$_3$ (10 g, manufactured by Kanto Chemical Co., Inc.) (the height of the filler: 34 mm) was used. The preheater and the fluidized bed were connected in series in a thermostat adjusted to a temperature of 270° C. to assemble a reactor, and the compound (15) obtained in the ester dissociation step was fed to the reactor while dry helium was passed through it. The compound (15) (0.0875 g) was fed intermittently at 5 minute intervals, and helium was fed at 50 mL/min. The compound (15) diluted with helium was fed to the fluidized bed through the preheater so that the retention time (contact time) of the compound (15) in the fluidized bed was 1.5 seconds. The resulting gas was recovered in a collector comprising a dry ice trap and a liquid nitrogen trap connected in series. The recovered sample was identified as the following compound (26) with a GC purity of 96% and a boiling point of 44.8° C. The conversion was 100%, and the yield was 55%. The $^{19}$F-NMR and GC-MS (the EI method) spectra agreed with those of an authentic sample.

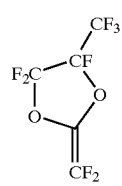
(26)

<Industrial Applicability>

The process for preparing a fluorinated acyl fluoride of the present invention permits efficient fluorination even if the starting material is an ether oxygen-containing compound and gives a good yield of a fluorinated acyl fluoride. The process for preparing a fluorinated vinyl ether of the present invention affords a fluorinated vinyl ether highly useful as a starting material for fluororesins. In the process of the present invention, choice of the structure of the starting compound makes it an industrially advantageous production process.

The entire disclosure of Japanese Patent Application No. 2000-229521 filed on Jul. 28, 2000 including specification, claims and summary is incorporated herein by reference in its entirety.

What is claimed is:

1. A process for preparing a fluorinated acyl fluoride represented by the following formula (3), which comprises reacting a compound represented by the following formula (1) having a fluorine content of 30 mass % or above with fluorine in a liquid phase to form a compound represented by the following formula (2) and then dissociating the ester bond in the compound represented by the formula (2):

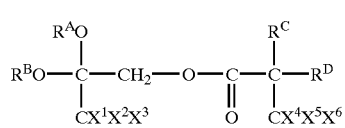
(1)

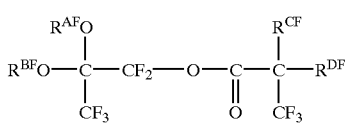
(2)

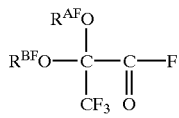
(3)

wherein each of $R^A$ and $R^B$, which may be the same or different, is a monovalent saturated hydrocarbon group, a halogenated monovalent saturated hydrocarbon group, a hetero atom-containing monovalent saturated hydrocarbon group or a halogenated (hetero atom-containing monovalent saturated hydrocarbon) group, each of $R^C$ and $R^D$, which may be the same or different, is a hydrogen atom, a halogen atom, a monovalent saturated hydrocarbon group, a halogenated monovalent saturated hydrocarbon group, a hetero atom-containing monovalent saturated hydrocarbon group or a halogenated (hetero atom-containing monovalent saturated hydrocarbon) group, each of $X^1$, $X^2$, $X^3$, $X^4$, $X^5$ and $X^6$, which may be the same or different, is a hydrogen atom or a fluorine atom, provided that at least one of $R^A$, $R^B$, $R^C$, $R^D$, $X^1$, $X^2$, $X^3$, $X^4$, $X^5$ and $X^6$ is a fluorine-containing group or a fluorine atom, $R^{AF}$ corresponds to $R^A$, $R^{BF}$ corresponds to $R^B$, $R^{CF}$ corresponds to $R^C$, $R^{DF}$ corresponds to $R^D$, and when $R^A$, $R^B$, $R^C$ and $R^D$ are hydrogen-containing groups, $R^{AF}$, $R^{BF}$, $R^{CF}$ and $R^{DF}$ are groups derived respectively from $R^A$, $R^B$, $R^C$ and $R^D$ by replacing substantially all the hydrogen atoms by fluorine atoms, and when $R^A$, $R^B$, $R^C$ and $R^D$ are groups containing no hydrogen atoms, $R^{AF}$, $R^{BF}$, $R^{CF}$ and $R^{DF}$ are the same as $R^A$, $R^B$, $R^C$ and $R^D$, respectively, the combination of $R^A$ and $R^B$ and the combination of $R^C$ and $R^D$ may form bivalent groups selected from bivalent saturated hydrocarbon groups, halogenated bivalent saturated hydrocarbon groups, hetero atom-containing bivalent saturated hydrocarbon groups and halogenated (hetero atom-containing bivalent saturated hydrocarbon) groups, respectively, the combination of $R^{AF}$ and $R^{BF}$ forms a bivalent group corresponding to a bivalent group formed by the combination of $R^A$ and $R^B$, and the combination of $R^{CF}$ and $R^{DF}$ forms a bivalent group corresponding to a bivalent group formed by the combination of $R^C$ and $R^D$, provided that when the combination of $R^A$ and $R^B$ and the combination of $R^C$ and $R^D$ form hydrogen-containing bivalent groups, the bivalent groups formed by the combination of $R^{AF}$ and $R^{BF}$ and the combination of $R^{CF}$ and $R^{DF}$ are groups derived from the hydrogen-containing bivalent groups by replacing substantially all the hydrogen atoms by fluorine atoms, and when the combination of $R^A$ and $R^B$ and the combination of $R^C$ and $R^D$ form bivalent groups containing no hydrogen atoms, the bivalent groups formed by the combination of $R^{AF}$ and $R^{BF}$ and the combination of $R^{CF}$ and $R^{DF}$ are the same as the bivalent groups containing no hydrogen atoms.

2. The process according to claim 1, wherein when the ester bond in the compound represented by the formula (2) is dissociated to form the fluorinated acyl fluoride represented by the formula (3), a compound represented by the following formula (4) is formed:

(4)

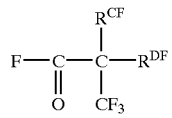

wherein $R^{CF}$ and $R^{DF}$ are the same as defined above.

3. The process according to claim 1, wherein the compound represented by the formula (1) is prepared by reacting a compound represented by the following formula (5) with a compound represented by the following formula (6):

(5)

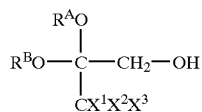

(6)

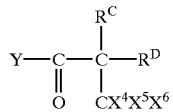

wherein $R^A$, $R^B$, $R^C$, $R^D$, $X^1$, $X^2$, $X^3$, $X^4$, $X^5$ and $X^6$ are the same as defined above, and Y is a halogen atom.

4. The process according to claim 1, wherein in the compound represented by the formula (2), $R^{CF}$ is the same as $OR^{AF}$, and $R^{DF}$ is the same as $OR^{BF}$.

5. The process according to claim 1, wherein the fluorine content of the compound represented by the formula (1) is from 30 to 70 mass %.

6. The process according to claim 1, wherein the molecular weight of the compound represented by the formula (1) is from 200 to 1000.

7. A process for preparing a fluorinated acyl fluoride represented by the following formula (3), which comprises reacting a compound represented by the following formula (5) with a compound represented by the following formula (7) to form a compound represented by the following formula (8) having a fluorine content of 30 mass % or above, fluorinating the compound represented by the formula (8) in a liquid phase to form a compound represented by the following formula (9) and dissociating the ester bond in the compound represented by the formula (9):

(5)

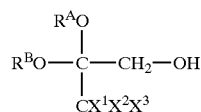

(7)

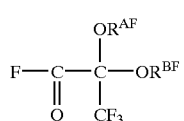

(8)

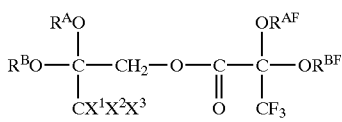

-continued (9)

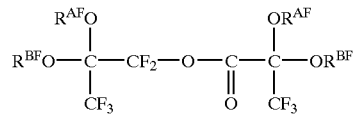

(3)

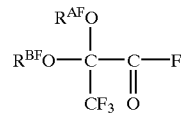

wherein each of $R^A$ and $R^B$, which may be the same or different, is a monovalent saturated hydrocarbon group, a halogenated monovalent saturated hydrocarbon group, a hetero atom-containing monovalent saturated hydrocarbon group or a halogenated (hetero atom-containing monovalent saturated hydrocarbon) group, each of $X^1$, $X^2$ and $X^3$, which may be the same or different, is a hydrogen atom or a fluorine atom, provided that at least one of $R^A$, $R^B$, $X^1$, $X^2$ and $X^3$ is a fluorine-containing group or a fluorine atom, $R^{AF}$ corresponds to $R^A$, $R^{BF}$ corresponds to $R^B$, and when $R^A$ and $R^B$ are groups containing a hydrogen atom, $R^{AF}$ and $R^{BF}$ are groups derived respectively from $R^A$ and $R^B$ by replacing substantially all of the hydrogen atoms by fluorine atoms, and when $R^A$ are $R^B$ are groups containing no hydrogen atoms, $R^{AF}$ and $R^{BF}$ are the same as $R^A$ and $R^B$, respectively, the combination of $R^A$ and $R^B$ may form a bivalent group selected from a bivalent saturated hydrocarbon group, a halogenated bivalent saturated hydrocarbon group, a hetero atom-containing bivalent saturated hydrocarbon group and a halogenated (hetero atom-containing bivalent saturated hydrocarbon) group, provided that when the combination of $R^A$ and $R^B$ forms a hydrogen-containing bivalent group, the bivalent group formed by the combination of $R^{AF}$ and $R^{BF}$ is a group derived from the hydrogen-containing bivalent group by replacing substantially all the hydrogen atoms by fluorine atoms, and when the combination of $R^A$ and $R^B$ forms a bivalent group containing no hydrogen atoms, the bivalent group formed by the combination of $R^{AF}$ and $R^{BF}$ is the same as the bivalent group containing no hydrogen atoms.

8. The process according to claim 7, wherein at least part of the compound represented by the formula (7) is a fluorinated acyl fluoride represented by the formula (3) obtained as the result of dissociation of the ester bond in the compound represented by the formula (9).

9. The process according to claim 7, wherein the fluorine content of the compound represented by the formula (8) is from 30 to 70 mass %.

10. The process according to claim 7, wherein the molecular weight of the compound represented by the formula (8) is from 200 to 1000.

11. The process according to claim 1, wherein all of $X^1$, $X^2$ and $X^3$ are hydrogen atoms.

12. The process according to claim 7, wherein all of $X^1$, $X^2$ and $X^3$ are hydrogen atoms.

13. The process according to claim 1, wherein $R^A$ and $R^B$ are hetero atom-containing monovalent saturated hydrocarbon groups which are ether oxygen-containing monovalent saturated hydrocarbon groups or halogenated (hetero atom-containing monovalent saturated hydrocarbon groups which are halogenated (ether oxygen-containing monovalent saturated hydrocarbon) groups.

14. The process according to claim 7, wherein $R^A$ and $R^B$ are hetero atom-containing monovalent saturated hydrocarbon groups which are ether oxygen-containing monovalent saturated hydrocarbon groups or halogenated (hetero atom-containing monovalent saturated hydrocarbon groups which are halogenated (ether oxygen-containing monovalent saturated hydrocarbon) groups.

15. A process for preparing a fluorinated vinyl ether, which comprises pyrolyzing the fluorinated acyl fluoride represented by the following formula (3) obtained by the process according to claim 1 to form a compound represented by the following formula (10):

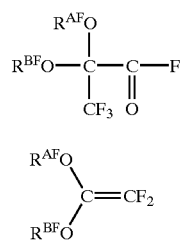

(3)

(10)

wherein $R^{AF}$ and $R^{BF}$ are the same as defined above.

16. A process for preparing a fluorinated vinyl ether, which comprises pyrolyzing the fluorinated acyl fluoride represented by the following formula (3) obtained by the process according to claim 7 to form a compound represented by the following formula (10):

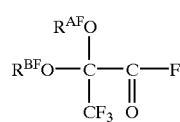

(3)

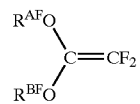

(10)

wherein $R^{AF}$ and $R^{BF}$ are the same as defined above.

17. A compound represented by the following formula (11) or (12):

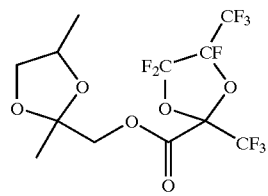

(11)

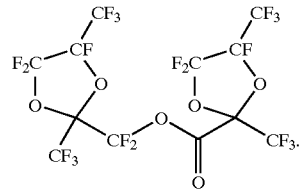

(12)

* * * * *

UNITED STATES PATENT AND TRADEMARK OFFICE
CERTIFICATE OF CORRECTION

PATENT NO. : 6,747,174 B2
DATED : June 8, 2004
INVENTOR(S) : Takashi Okazoe et al.

It is certified that error appears in the above-identified patent and that said Letters Patent is hereby corrected as shown below:

Column 26,
Line 65, "containing monovalent saturated hydrocarbon groups ..." should read
-- containing monovalent saturated hydrocarbon) groups ... --.

Column 2,
Line 5, "containing monovalent saturated hydrocarbon groups ..." should read
-- containing monovalent saturated hydrocarbon) groups ... --.

Signed and Sealed this

Thirtieth Day of May, 2006

JON W. DUDAS
*Director of the United States Patent and Trademark Office*